United States Patent [19]
Pisharodi

[11] Patent Number: 5,658,336
[45] Date of Patent: Aug. 19, 1997

[54] ROTATING, LOCKING, MIDDLE-EXPANDED INTERVERTEBRAL DISK STABILIZER

[76] Inventor: Madhavan Pisharodi, 942 Wild Rose La., Brownsville, Tex. 78520

[21] Appl. No.: 475,211

[22] Filed: Jun. 7, 1995

Related U.S. Application Data

[63] Continuation-in-part of PCT/US95/03347, Mar. 17, 1995, and Ser. No. 210,229, Mar. 18, 1994.

[51] Int. Cl.$^6$ .................................................. A61F 2/44
[52] U.S. Cl. ........................ 623/17; 623/66; 606/61; 606/73
[58] Field of Search ................. 606/61, 62, 63, 606/60, 53, 66, 73; 623/17, 66

[56] References Cited

U.S. PATENT DOCUMENTS

| | | | |
|---|---|---|---|
| 3,334,624 | 8/1967 | Schmeider et al. | 606/62 |
| 3,486,505 | 12/1969 | Morrison | 128/303 |
| 4,349,921 | 9/1982 | Kuntz | 3/1 |
| 4,657,550 | 4/1987 | Daher | 623/17 |
| 4,696,290 | 9/1987 | Steffee | 606/73 |
| 4,711,232 | 12/1987 | Fischer et al. | 128/92 |
| 4,759,769 | 7/1988 | Hedman et al. | 623/17 |
| 4,834,757 | 5/1989 | Brantigan | 623/17 |
| 4,863,476 | 9/1989 | Shepperd | 623/17 |
| 4,932,975 | 6/1990 | Main et al. | 623/17 |
| 5,015,247 | 5/1991 | Michelson | 606/61 |
| 5,059,193 | 10/1991 | Kuslich | 606/61 |
| 5,129,899 | 7/1992 | Small et al. | 606/61 |
| 5,171,278 | 12/1992 | Pisharodi | 623/17 |
| 5,306,309 | 4/1994 | Wagner et al. | 606/61 |
| 5,324,292 | 6/1994 | Meyers | 606/73 |
| 5,401,269 | 3/1995 | Buttner-Janz et al. | 623/17 |
| 5,443,514 | 8/1995 | Steffee | 623/17 |
| 5,505,732 | 4/1996 | Michelson | 606/61 |

FOREIGN PATENT DOCUMENTS

| | | |
|---|---|---|
| 2151481 | 3/1995 | Canada . |
| 0042271 | 12/1981 | European Pat. Off. . |
| 0260044 | 3/1988 | European Pat. Off. . |
| 0307241 | 3/1989 | European Pat. Off. . |
| 3505567 | 6/1986 | Germany . |
| 3729600 | 3/1989 | Germany . |
| 0662082 | 2/1982 | U.S.S.R. . |
| WO9214423 | 9/1992 | WIPO . |
| WO9508306 | 3/1995 | WIPO . |
| WO9526164 | 10/1995 | WIPO . |

*Primary Examiner*—Paul B. Prebilic
*Attorney, Agent, or Firm*—Mark R. Wisner

[57] ABSTRACT

A middle expanded, removable disk implant for stabilizing adjacent vertebrae. The implant is substantially rectangular in cross-sectional shape with a minimal height and a width greater than the height. The implant is detachably mounted to an applicator for insertion into the anatomical region between two adjacent vertebrae from which a portion of the intervertebral disk has been removed, and once inserted, is positioned by anterior-posterior movement in the disk space to the position in which both the expanded, larger width middle portion and the smaller diameter end portions of the implant will engage the bodies of the adjacent vertebrae and the implant is then rotated to bring the sides of the rectangularly-shaped implant defining the width of the implant, with its larger dimension, into engagement with the bodies of the adjacent vertebrae. A lock is then secured to the implant to prevent further rotation thereof.

11 Claims, 2 Drawing Sheets

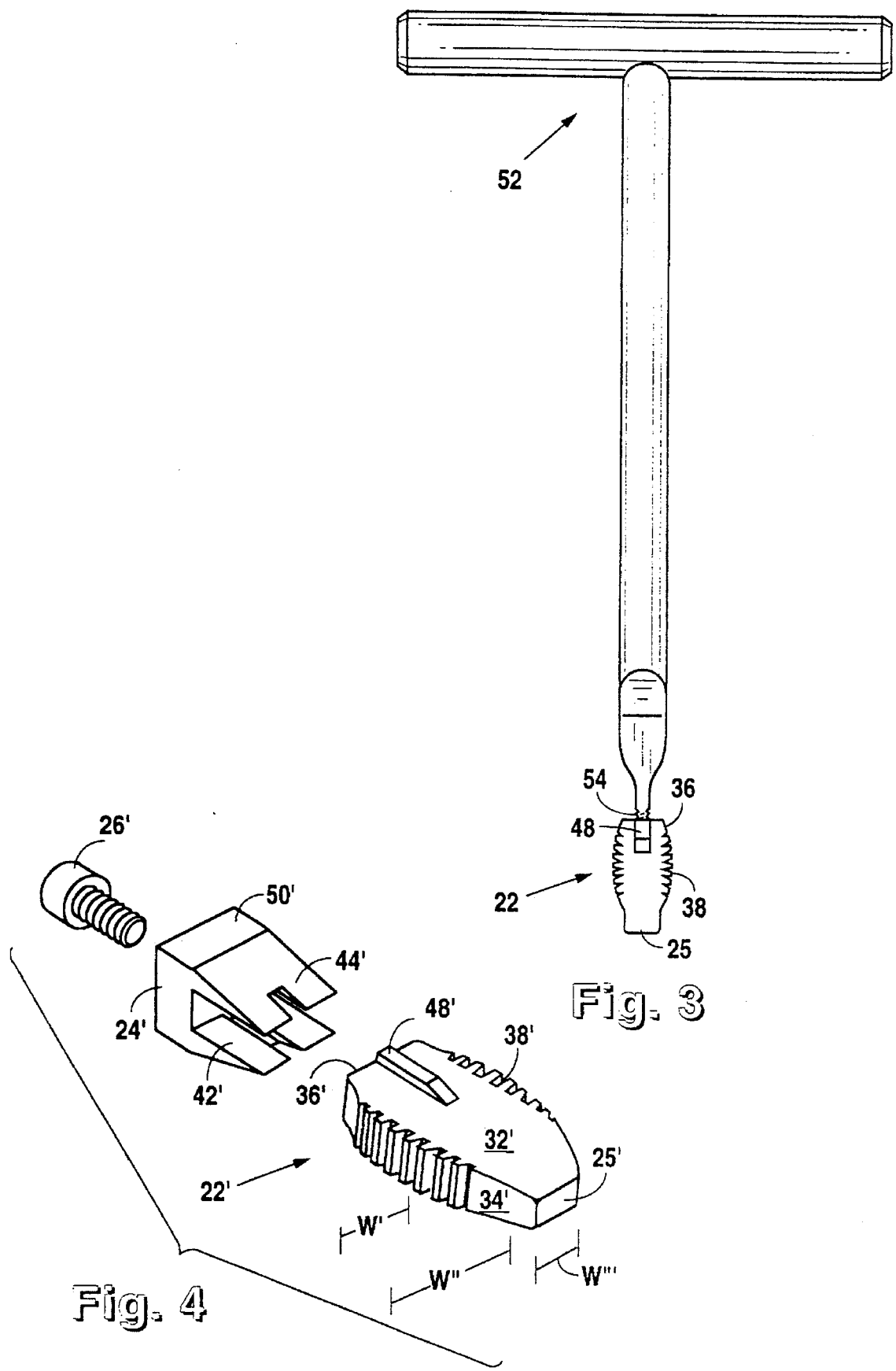

ROTATING, LOCKING, MIDDLE-EXPANDED INTERVERTEBRAL DISK STABILIZER

CROSS REFERENCE TO RELATED APPLICATION

The present application is a continuation-in-part of the U.S. National Phase application to be filed on International Application No. PCT/US95/03347 entitled MIDDLE EXPANDED, REMOVABLE, INTERVERTEBRAL DISK IMPLANT AND METHOD OF LUMBAR INTERVERTEBRAL DISK STABILIZATION filed on Mar. 17, 1995. When filed in the U.S., that National Phase application will itself be a continuation-in-part of U.S. application Ser. No. 08/210,229, filed Mar. 18, 1994, and having that same title.

BACKGROUND OF THE INVENTION

The present invention relates to an intervertebral disk stabilizing implant and a method of stabilizing two adjacent vertebrae. More specifically, the present invention relates to rectangularly-shaped disk implants which are expanded in the middle portion and are used for spinal fusion.

Treatment of a herniated disk in the neck and in the lumbar region continues to be a challenging field of medicine. The classical treatment for a ruptured disk is diskectomy, i.e., removal of the disk from between the vertebrae. In this process, all or a portion of the intervertebral disk is removed, leaving a defect which continues to bother the patients throughout the rest of their lives. An additional procedure is to replace the disk space with a bone graft, usually bone chips cut from the patient's iliac crest, bringing about fusion of the vertebrae above and below the disk, eliminating the empty space between the vertebrae.

Diskectomy with fusion is not ideal because the replaced bone does not have the function of the cartilaginous tissue of the disk, i.e. no cushioning effect, and has complications because of several factors. First, conventional bone plugs used to pack the disk space do not conform to the space of the disk because the disk bulges maximally in the center. The disk space is wider in the middle and narrower at its anterior and posterior ends. For this reason, the various bone plugs which are currently available commercially have only four contact points, i.e. at the front and back of the disk space. Secondly, access to the disk is from the side of the dorsal spine of the adjacent vertebrae, leaving a space that is "off-center" relative to the bodies of the adjacent vertebrae such that the stability of the implant is even more problematical than might be apparent from the limited contact resulting from the shape of the intervertebral space. Another complication is the possibility of infection or other conditions which may require the removal of the implant. Also, if the bone pieces do not fuse, they may eventually extrude out of the disk space, causing pressure on the nerve roots.

Various prosthetic disk plugs, or implants, are disclosed in the art, but all are characterized by limitations of not conforming to the shape of the disk space, lack of stability when inserted off-center, inability to be removed, or other disadvantages. For instance, U.S. Pat. No. 4,863,476 (and its European counterpart, EP-A-0260044) describes an elongated body divided longitudinally into two portions having a cam device movable therebetween for increasing the space between the two body portions once inserted into the disk space. However, that device is generally cylindrical in shape such that the only contact points between the device and the vertebral bodies are at the front and back of the disk space, creating increased likelihood of instability and generally rendering that device unsuitable for use after partial diskectomy. The art also discloses intervertebral disk prostheses (e.g., U.S. Pat. Nos. 3,867,728, 4,309,777, 4,863,477 and 4,932,969 and French Patent Application No. 8816184) which may have more general contact with the adjacent disks, but which are not intended for use in fusion of the disks. The art also includes spinal joint prostheses such as is described in U.S. Pat. No. 4,759,769, which is again not indicated for use when fusion is the preferred surgical intervention.

There is, therefore, a need for a device capable of stabilizing the vertebrae adjacent an intervertebral disk, but which is also, removable, for use in spinal fusion. There is also a need for a method of implanting such a stabilizer.

SUMMARY OF THE INVENTION

These needs are met in the present invention by providing a vertebral disk stabilizer comprising an elongate implant having first, second, third and fourth sides providing the implant with a substantially rectangular cross-sectional shape of minimal height defined by the first and second sides and maximal width defined by the third and fourth sides, the third and fourth sides being arched from one end of the implant to the other to provide the portion intermediate the ends with a width larger than the width of the implant at the ends thereof. A lock having a bearing surface formed thereon is detachably mounted to one end of the implant to prevent rotation of the lock relative to the implant with the bearing surface oriented at approximately 90° to the height of the implant.

Also provided is a method of stabilizing two adjacent vertebrae after removing a portion of the intervertebral disk from therebetween to form a disk space comprising the steps of inserting a substantially rectangularly-shaped, elongate implant having a width greater than its height into the disk space with the implant oriented so that the top and bottom thereof engage the bodies of the adjacent vertebrae, rotating the implant approximately 90° in the disk space to contact the bodies of the adjacent vertebrae with the sides of the implant, and securing a lock to the implant to prevent rotation of the implant relative to the lock. The lock is provided with a surface for bearing against the body of the adjacent vertebrae to prevent rotation of the lock relative to the body of the adjacent vertebrae against which the surface of the lock bears.

BRIEF DESCRIPTION OF THE DRAWINGS

FIG. 3 is a top plan view of the implant of FIG. 1 having a handle mounted thereto in place of the lock shown in FIG. 2.

FIG. 4 is an exploded, perspective view of a second preferred embodiment of the vertebral disk stabilizer of the present invention.

DETAILED DESCRIPTION OF THE PREFERRED EMBODIMENTS

Figure 1:
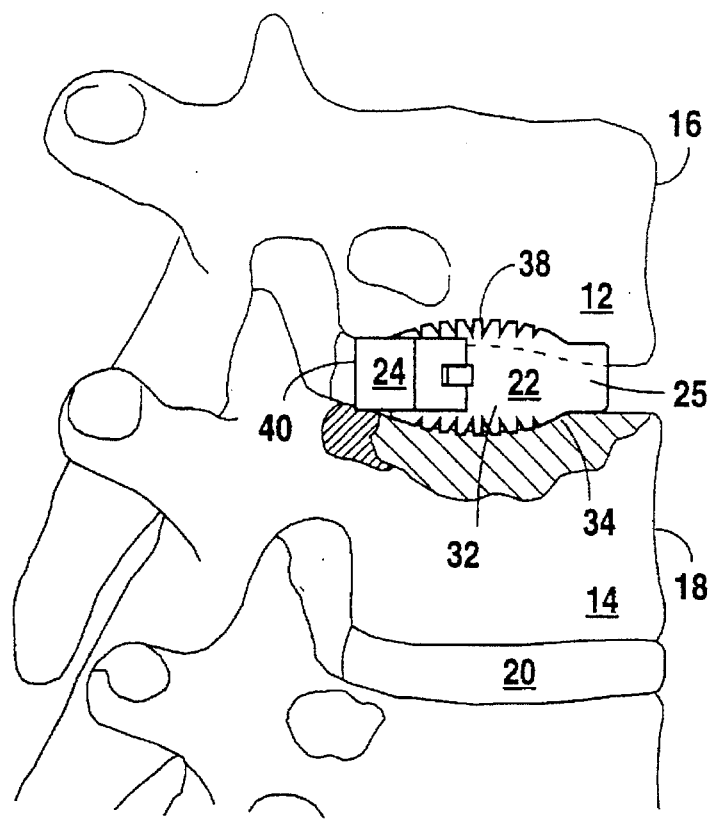
FIG. 1 is a lateral view of a portion of a human spinal column having a preferred embodiment of vertebral disk stabilizer of the present invention inserted therein and having a portion of the bodies of the vertebrae adjacent the implant shown cut away and/or in shadow lines to show the engagement of the vertebral bodies by the vertebral disk stabilizer.

Referring now to the figures, a first embodiment of a disk stabilizer constructed in accordance with the teachings of the present invention is shown implanted in a human spinal column in FIG. 1. The vertebral disk stabilizer, indicated generally at reference numeral 10, is implanted between the bodies 12 and 14 of two adjacent vertebrae 16 and 18, respectively, in the disk space (not numbered) from which a portion of the intervertebral disk 20 is removed, i.e. by simple diskectomy and small laminotomy.

Figure 2:
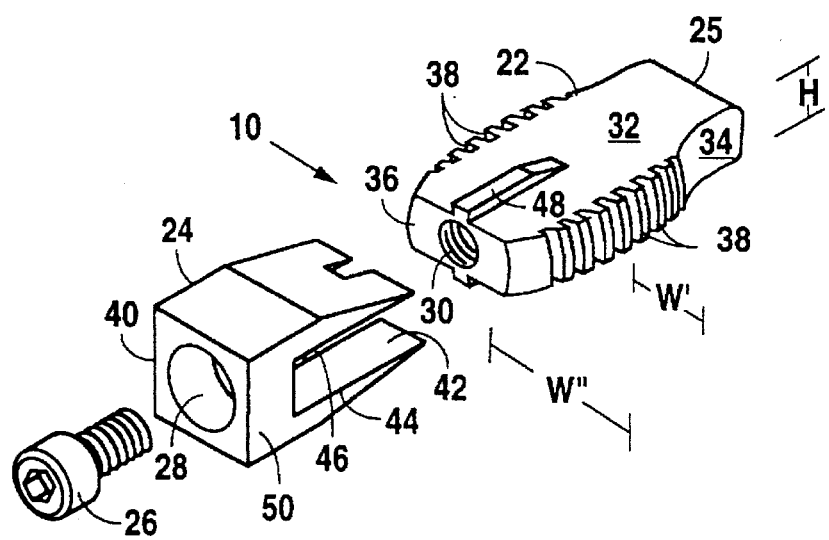
FIG. 2 is an exploded, perspective view of the vertebral disk stabilizer of FIG. 1.

Referring now also to FIG. 2, the vertebral disk stabilizer 10 is comprised of an elongate implant 22, lock 24, and means for detachably mounting the lock 24 to one end 25 of the implant 22. In the presently preferred embodiment shown, the mounting means. takes the form of a bolt 26 passing through a bore 28 in lock 24, the threads of bolt 26 engaging complementary threads in the walls of the bore 30 in the end 25 of implant 22.

In more detail, implant 22 is comprised of first and second sides 32 and third and fourth sides 34 providing a substantially rectangularly-shaped cross-section. The height H of the rectangularly shaped cross-section is defined by first and second sides 32 and the width W is defined by the third and fourth sides 34 and, as is apparent by comparison of H and W, the height of H of implant 22 is less than the width W. As will be explained below, H is minimized to facilitate insertion of the second end 36 into, and positioning of implant 22 in, the disk space from which a portion of the intervertebral disk 20 was removed and W is maximized to provide the desired stabilization to adjacent vertebrae 16 and 18. Third and fourth sides 34 are arched from one end of implant 22 to the other to provide the portion of implant 22 intermediate the ends 25 and 36 with a width W' which is larger than the width W" at the ends 25 and 36. Because the sides 32 of implant 22 are substantially flat and the sides 34 are arched from one end 25 to the other end 36, implant 22 is described as being a biplanar, hi-convex implant. The bi-convex sides 34 of implant 22 are provided with a plurality of teeth 38 for biting into the adjacent vertebrae 16 and 18 as will be explained in more detail below. The end 36 of implant 22 is formed in a blunt, or rounded shape to reduce the likelihood of injury to the nerves of the spinal cord during insertion into the disk space.

In the preferred embodiment shown, lock 24 is substantially square when viewed from the end 40 along the axis of the bore 28 therethrough and U-shaped when viewed from the side. The inside surfaces 42 of the arms 44 of the U-shaped lock 24 are flat for contacting the first and second sides 32 of implant 22 to prevent rotation of lock 24 relative to implant 22 when lock 24 is mounted to implant 22 and secured thereto by bolt 26. The surfaces 42 are provided with a slot 46 for receiving a complementary-shaped key 48 to facilitate assembly of lock 24 to implant 22; those skilled in the art who have the benefit of this disclosure will recognize that the slot 46 may be located on the implant 22 and the key 48 may be located on the lock 24 without any difference in the manner in which those component parts function. The bore 28 in lock 24 is aligned with the bore 30 in implant 22.

The sides of the square end 40 of lock 24 provide surfaces 50 for bearing against the bodies 12 and 14 of adjacent vertebrae 16 and 18 as also explained in more detail below. It will be recognized by those skilled in the art who have the benefit of this disclosure that the bearing surfaces 50 need not be flat and that the end 40 of lock 24 need not be square. Other shapes and configurations may be utilized as needed to insure that movement of lock 24 is limited by the bodies of the adjacent vertebrae 16 and 18. The purpose of the hi-planar, middle expanded, hi-convex implant 22 is to enable insertion of the implant 22 into the disk space and turning by approximately 90° to increase the disk height and stabilize the disk space. The purpose of lock 24 is to lock implant 22 against instability when in the vertical position so as to maintain the disk height thereafter.

Referring now to FIG. 3, there is shown an applicator 52 mounted to the end 25 of implant 22. In the embodiment shown, applicator 52 is mounted to implant 22 by screwing the threaded end 54 thereof into the threaded bore 30 in implant 22. When the end 54 of applicator 52 is screwed all the way into the bore 30, so as to prevent relative movement therebetween, implant 22 is inserted into the disk space and rotated therein using applicator 52 as explained below. Applicator 52 is detached from implant 22 by rotating in the opposite direction while rotation of implant 22 is restrained.

The use of the stabilizer 10 of the present invention in, for instance, a method of lumbar intervertebral disk stabilization, or "LIDS," is illustrated in FIG. 1. Surgery is performed as in a simple diskectomy and the intervertebral disk 20 is exposed through a small laminotomy. The disk material is removed and any nerve root compression is corrected. The posterior longitudinal ligament (not shown) and disk cartilage are removed until the surface of the bodies 12 and 14 of adjacent vertebrae 16 and 18, respectively, are exposed above and below the disk space.

Using spreaders such as those disclosed in International Application No. PCT/US95/00347, which reference is hereby incorporated into this specification in its entirety by this specific reference thereto, the vertebrae 16 and 18 are distracted to open the disk space, and once the desired "spread" is achieved, the middle portion of the disk space is packed with cancellous bone chips (not shown). Because the posterior longitudinal ligament is left intact to the opposite side and to the center of the disk space, the bone chips are held in place in the disk space.

An implant 22 having a height H and width W selected to fit the disk space is then mounted on applicator 52 by screwing on to the threaded end 54. The appropriately-sized implant 22 is then inserted into the disk space using the applicator 52 with the implant 22 oriented so that the top and bottom thereof, i.e., the first and second sides 32, engage the bodies 12 and 14 of adjacent vertebrae 16 and 18, respectively. Using the applicator 52, implant 22 is then moved further into (or back out of) the disk space in an anterior-posterior direction so as to enable the implant 22 to be positioned in the disk space at a position in which the expanded, middle portion and the smaller width ends 25 and 36 of the third and fourth sides 34 of implant 22 contact the respective lower and upper surfaces of the bodies 12 and 14 of the adjacent vertebrae 16 and 18 when rotated by approximately 90° using the applicator 52. The respective lower and upper surfaces of the vertebral bodies 12 and 14 are slightly concave such that the larger width middle portion W" of implant 22 allows the implant 22 to engage substantially more of the respective surfaces of the vertebral bodies 12 and 14 than conventional prosthetic devices, thereby providing increased stability to the fusion once further rotation of implant 22 in the disk space is prevented as described below.

Once positioned in the disk space so as to provide maximum stabilization, the applicator 52 is then detached from the implant 22 by unscrewing and backed out of the incision in the patient. Lock 24 is then inserted through that same incision and, using the slot 46 and key 48, the bore 28 in lock 24 and bore 30 in implant 22 are aligned and the bolt 26 is inserted and tightened to secure lock 24 to the implant 22. Securing the lock 24 to implant 22 in this manner prevents relative rotation between lock 24 and implant 22 and the bearing surfaces 50 of lock 24 bear against the bodies 12 and 14 of the adjacent vertebrae 16 and 18 to prevent rotation of the lock 24 relative to the adjacent vertebrae 16 and 18 against which the bearing surfaces 50 bear. Those skilled in the art who have the benefit of this disclosure will recognize that the bearing surfaces 50 bear against the cortical end plate of the respective vertebral bodies 12 and 14, which is comprised of non-cancellous bone, and provides a hard, relatively smooth surface against which the bearing surfaces 50 bear. The end 40 of lock 24 is preferably supplied in a plurality of different sizes and shapes other than the square shaped end 40 shown in the figures so as to allow the surgeon to select an appropriately sized and shaped lock which provides a close fit with the space between vertebral bodies.

If necessary, a small amount of a physiologically compatible adhesive of a type known in the art is applied over the cancellous bone chips just medial to the implant to close off the remaining portion of the opening into the disk space. The patient should be able to ambulate soon after the LIDS procedure because of the stability imparted to the spinal column by the implant of the present invention. Before narrowing of the disk space occurs, the cancellous bone chips will have started the fusion process.

The stabilizer 10 is also used to advantage to perform, for instance, a posterior lateral intertransverse fusion. The implant 22 is inserted into the region of the disk space from which a portion of the disk has been removed as described above with the lock 24 and the posterior lateral fusion performed. Because the implant 22 provides stability to the spine until the posterior lateral fusion is solid, the patient is generally able to ambulate soon after surgery. This procedure also prevents the narrowing of the disk space, which is a common problem with posterior lateral fusion.

Removal of the implant 22 is accomplished with relative ease compared to conventional implants. The bolt 26 is screwed back out of implant 22 and lock 24 is pulled out of the disk space. Applicator 52 is re-inserted and screwed into the bore 30 in implant 22 and used to rotate implant 22 by approximately an additional 90°, causing the first and second sides, having minimal height, to contact the bodies 12 and 14 of adjacent vertebrae 16 and 18 so as to allow posteriorly-directed movement of the implant 22 out of the disk space.

Although described in terms of the preferred embodiment shown in the figures, this embodiment is shown to exemplify the present invention, it being recognized by those skilled in the art that certain changes can be made to the specific structure of the preferred embodiment shown and described without departing from the spirit of the present invention. Such a change is shown in FIG. 4 in which the first and second sides 32' of implant 22' are substantially flat but not parallel along their longitudinal axes. The wedge shape of the implant 22' facilitates insertion of the implant 22' into the disk space, the rounded end 36 reducing the likelihood of injury to the nerves of the spinal cord during insertion into the disk space. Likewise, comparison of the widths W', W", and W'" of implant 22' will show that the width W' of implant 22' at the end 36' is less than the width W'" at the end 25', both widths, however, being less than the width W" in the middle, expanded portion of implant 22'. Further, the connection by which lock 24 is mounted to implant 22 is capable of being constructed in a manner different than that shown in the figures herein. Another such modification relates to the teeth 38 formed on the sides 34 of implant 22. So as to provide additional resistance to forward or backward movement of implant 22 in the disk space, the teeth 38 located closest to the end 25 of implant 22 (e.g., the teeth in the distal portion of implant 22) may be oriented at a slant toward the end 25 and the teeth 38 closest to the end 36 of implant 22 may be oriented at a slant toward the end 36. The teeth in the middle portion of implant 22, e.g., between the two sets of slanted teeth, are then oriented vertically. All such modifications, and other modifications which do not depart from the spirit of the present invention, are intended to fall within the scope of the following claims.

What is claimed is:

1. A vertebral disk stabilizer comprising:

an elongate implant having a substantially rectangular cross-sectional shape perpendicular to the elongate length thereof, comprised of first, second, third, and forth sides providing a minimal height defined by the first and second sides and maximal width defined by the third and forth sides, the third and forth sides being arched from one end of said implant to the other end of said implant to provide the middle portion of said implant with a bi-convex shape having a width larger than the width of the ends of said implant, the height being less than the width;

a lock having a bearing surface formed thereon, and means detachably mounting said lock to one end of said implant to prevent rotation of said lock relative said implant with the bearing surface oriented at approximately 90° with respect to the height of said implant.

2. The stabilizer of claim 1 wherein the third and fourth sides of said implant are provided with teeth.

3. The stabilizer of claim 1 wherein said lock is provided with a substantially flat surface for contacting either the first or the second side of said implant to prevent rotation of said lock relative to said implant.

4. The stabilizer of claim 1 wherein the corners of said implant between the first, second, third, and fourth sides are rounded.

5. The stabilizer of claim 1 wherein the end of said implant opposite the end to which said lock is mounted is rounded.

6. The stabilizer of claim 1 additionally comprising an applicator for detachably mounting to said implant after removing said lock therefrom.

7. Apparatus for inserting between adjacent vertebrae after removal of a portion of the intervertebral disk from therebetween with an elongate applicator comprising:

an elongate implant having a substantially rectangular cross-sectional shape perpendicular to the elongate length thereof, comprised of first and second substantially flat sides defining the height of said implant and third and fourth sides defining the width of said implant, the third and fourth sides being arched to provide said implant with a bi-convex shape having a width greater in the middle portion than at the ends thereof, the height of said implant being less in dimension than the width of said implant;

means formed in one end of said implant for detachably mounting an applicator to said implant; and a lock detachably secured to said implant to prevent rotation of said implant in the space between the adjacent vertebrae after (a) inserting said implant when mounted to said applicator into the space between the adjacent vertebrae with the first and second sides of said implant contacting the adjacent vertebrae, (b) rotating said applicator having said implant mounted to the applicator approximately 90° to cause the third and fourth sides of said implant to contact the adjacent vertebrae, and (c) detaching said applicator from said implant.

8. The apparatus of claim 7 wherein said lock is provided with a surface for bearing against the adjacent vertebrae to prevent rotation of said lock relative to the adjacent vertebrae.

9. The apparatus of claim 8 wherein said bearing surface is oriented at an angle of approximately 90° to the first and second sides of said implant when secured thereto.

10. The apparatus of claim 7 wherein said lock is provided with a flat surface for contacting either the first or second surface of said implant when secured thereto.

11. The apparatus of claim 7 wherein the third and fourth sides of said implant are provided with teeth for biting into the adjacent vertebrae when said implant is rotated.

* * * * *